United States Patent [19]

Kelman

[11] Patent Number: 4,596,578
[45] Date of Patent: Jun. 24, 1986

[54] INTRAOCULAR LENS WITH MINIATURE OPTIC

[76] Inventor: Charles D. Kelman, North Shore Towers - 269 Grand Central Pkwy., Bldg. 3, Floral Park, N.Y. 11005

[21] Appl. No.: 575,018

[22] Filed: Jan. 30, 1984

[51] Int. Cl.4 ............................................... A61F 2/16
[52] U.S. Cl. ....................................................... 623/6
[58] Field of Search ................................... 3/13; 623/6

[56] References Cited

U.S. PATENT DOCUMENTS

| 4,056,855 | 11/1977 | Kelman | 3/13 |
| 4,118,808 | 10/1978 | Poler | 3/13 |
| 4,168,547 | 9/1979 | Konstantinov et al. | 3/13 |
| 4,172,297 | 10/1979 | Schlegel | 3/13 |
| 4,174,543 | 11/1979 | Kelman | 3/13 |

*Primary Examiner*—Ronald L. Frinks
*Attorney, Agent, or Firm*—Henry Sternberg; Bert J. Lewen

[57] ABSTRACT

An intraocular lens having an optic which has a dimension, determinative of the smallest incision through which it can be inserted, of substantially less than 5 mm and which includes a mask overlying a peripheral marginal portion of the optic for preventing glare.

12 Claims, 8 Drawing Figures

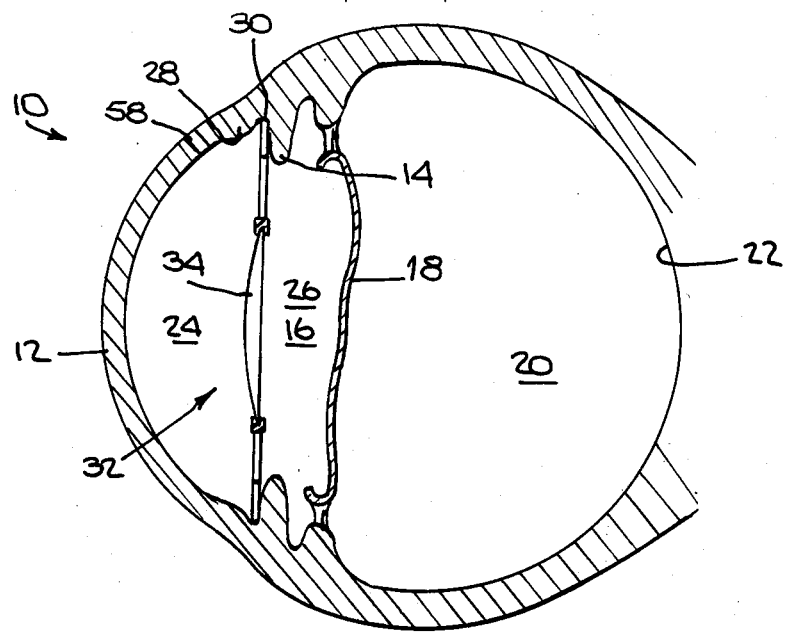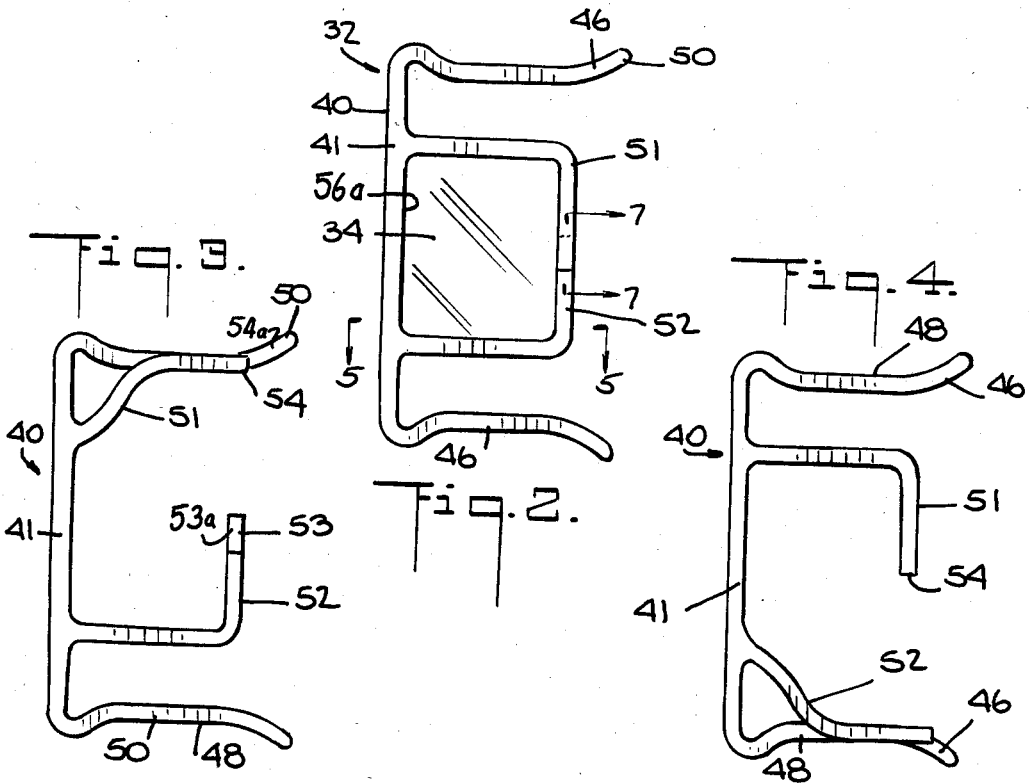

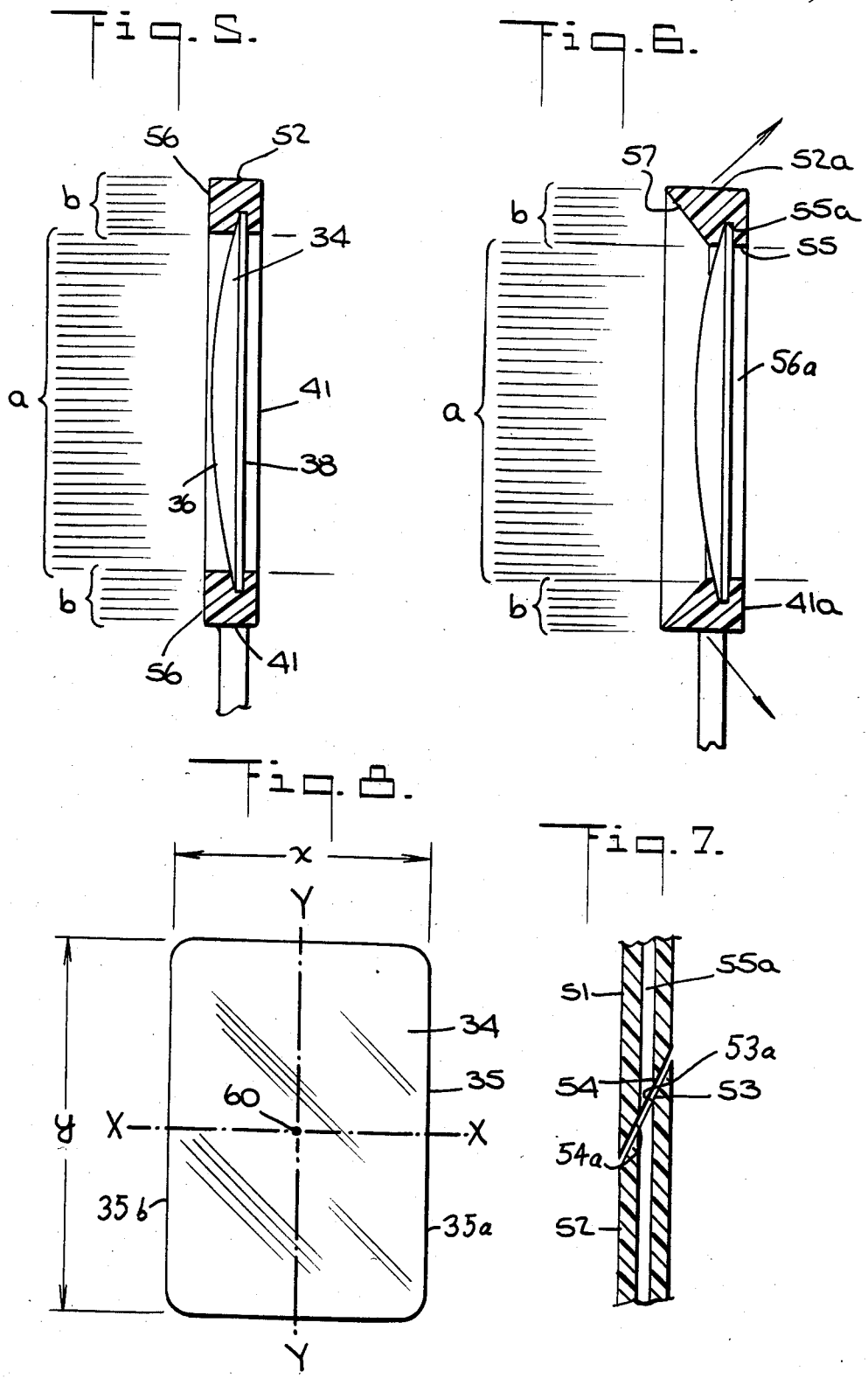

INTRAOCULAR LENS WITH MINIATURE OPTIC

This invention relates to intraocular lenses for the human eye, and, more particularly, to intraocular lenses of the type which can be positioned in the anterior chamber, the posterior chamber, or partially in the anterior chamber and partially in the posterior chamber of the eye. The invention also relates to methods of inserting and positioning such lenses in an eye.

One type of intraocular lens is described and claimed in my U.S. Pat. No. 4,174,543 issued Nov. 20, 1979. Such a lens is inserted into the eye through a corneoscleral incision that may be also used to remove a natural lens. To minimize the possibility of injury to the eye, it is important that the incision be made as small as possible. To this end, another type of lens is described and claimed in my co-pending application Ser. No. 422,374, now U.S. Pat. No. 4,451,935 entitled Intraocular Lens and Method of Positioning the Same in an Eye. In my co-pending application a lens is described and claimed which has a two-piece optic, allowing the surgeon to make an incision in the eye smaller than the diameter of the lens body, or optic. In the case of the two-piece optic, depending on where the optic is split and depending on the means used for connecting the two pieces together there may result in some instances an undesirable glare effect at the juncture of the two pieces. This same undesirable glare effect has in the past precluded the use of intraocular lenses with optics substantially smaller than 5 mm in diameter, due to the peripheral marginal regions of the miniature optic being in the path of light rays directed toward the retina.

It is an object of the present invention, therefore, to provide a new and improved intraocular lens which avoids one or more of the limitations of prior such lenses.

It is another object of the invention to provide a new and improved intraocular lens which has a lens body which is smaller than the lens body of conventional lenses yet which does not result in undesirable glare.

It is another object of the invention to provide a new and improved method of positioning an intraocular lens in an eye, which avoids one or more of the limitations of prior such methods.

It is another object of the invention to provide a new and improved method of positioning an intraocular lens in an eye utilizing a smaller incision in the eye than the incision required for insertion of a conventional intraocular lens into the eye.

In accordance with the invention, an intraocular lens comprises a lens body and a position-fixation means extending from the lens body for fixating the position of the lens body within the eye. The position fixation means includes masking means for preventing glare from a marginal peripheral portion of the lens body. The lens body and the position-fixation means are separable from one another outside the eye, are individually insertible through an opening in the eye, and are connectable within the eye to form the lens. The lens has a miniature lens body i.e. a lens body which has at least one small dimension which permits it to be inserted into the eye through an incision which is substantially smaller than the incision now generally required for insertion of conventional lens bodies.

Also in accordance with the invention, a method of positioning in an eye an intraocular lens having a plurality of portions which are separable outside the eye and connectable inside the eye, the lens portions including the lens body and the position-fixation member, said position-fixation member having a central stem portion, a pair of opposite seating portions extending generally transversely from opposite ends of said stem portion and a pair of arms also extending generally transversely from spaced regions of said stem portion intermediate said seating portions, each of said arms being flexible so as to be deflectable from a first position in which said arm substantially overlies a peripheral marginal region of said lens body to a second position in which the free end of said arm is closer to the adjacent one of said seating portions than in said first position thereof. The method includes inserting one of said seating portions of the position-fixation member through an incision in the eye while holding the corresponding arm in its second position thereof, inserting the stem portion of the position-fixation member through the incision, and finally inserting the other of said seating portions through the incision while holding the other arm in its second position thereof closer to said other seating portion than in said first position thereof. The method also includes inserting a miniature lens body through the opening in the eye, and connecting the lens body to the position-fixation means within the eye to form the lens.

For a better understanding of the present invention, together with other and further objects thereof, reference is made to the following description, taken in connection with the accompanying drawings, and its scope will be pointed out in the appended claims.

Referring now to the drawings:

FIG. 1 is a simplified schematic sectional view of an eyeball implanted with an intraocular lens embodying a preferred form of the present invention;

FIG. 2 is a plan view of the intraocular lens represented in FIG. 1;

FIG. 3 is a plan view of the position-fixation member of the lens of FIGS. 1 and 2 shown with one of its arms in position for insertion into the eye;

FIG. 4 is a plan view of the position-fixation member of the lens of FIGS. 1 and 2 showing the other of its arms in position for insertion into the eye;

FIG. 5 is a transverse sectional view along line 5—5 of FIG. 2;

FIG. 6 is a transverse sectional view similar to the view in FIG. 5, of another embodiment of a lens constructed in accordance with the invention;

FIG. 7 is a partial transverse sectional view along line 7—7 of FIG. 2; and

FIG. 8 is a plan view of a lens body according to the present invention.

Referring now particularly to FIGS. 1 and 2 of the drawings, reference 10 generally designates an eyeball shown in simplified schematic cross-section in FIG. 1. Portions of the eyeball structure which are not believed to be essential to an understanding of the invention have been omitted for the sake of clarity.

The eyeball 10 includes a cornea 12, an iris 14 having a central opening or pupil 16, a membrane 18, vitreous humor 20 and a retina 22. The natural lens, which normally occupies part of the region between the membrane 18 and the iris 14, has been omitted since the invention deals with artificial substitutes for a natural lens. An aqueous zone, between the cornea 12 and the membrane 18, is subdivided by the iris 14 into an anterior chamber 24 and a posterior chamber 26. A scleral spur 28 in the anterior chamber 24 is spaced from the iris 14 thereby defining a groove 30.

An intraocular artificial lens for the eyeball 10 is generally indicated by reference numeral 32 in FIG. 1 and will first be described generally with reference to FIGS. 1 and 2. The lens 32 can be formed of any suitable material compatible with the environment of the eyeball, such as a non-toxic plastic, for example, polymethylmethacrylate.

The lens 32 includes a medial light-focusing lens body 34, or optic, having, for example, a convex anterior surface 36 and a generally flat posterior surface 38 and having a pair of imaginary coordinate axes perpendicular to each other and to the optical axis of the lens body. While optics of conventional intraocular lenses are generally round and 5 to 6 mm in diameter, the optic, or lens body, according to the present invention may be of any suitable shape, for example, round, oval or rectangular, but has a maximum dimension along at least one of said coordinate axes substantially less than 5 mm, i.e. substantially less than the corresponding dimension of a conventional intraocular lens optic.

The lens 32 further includes a position fixation member 40 having a main stem portion 41 having at opposite ends thereof a pair of identical limb portions 46, 46 joined thereto in cantilever arrangement and having concave outer seating edges 48 terminating in contact lobes 50, 50.

Referring now more particularly to FIGS. 3 and 4, the position-fixation member 40 will be described in greater detail. The position-fixation member 40 comprises, in addition to the pair of integral limb portions 46, 46, a pair of integral oppositely disposed symmetrical arm portions 51 and 52 preferably of dog-leg shape. The arm portion 51 is connected at one end thereof to an intermediate portion of the stem 41 and has an opposite free end 54. Arm portion 52 is connected at one end with a spaced intermediate portion of stem 41 and has an opposite free end 53 adapted to engage free end 54 of arm 51 when the arms are in the closed, undeformed, position thereof, shown in FIG. 2. Arms 51 and 52 each preferably have a grooved inner surface 55 for surrounding and securely retaining therein a lens body 34. Groove 55a is shaped so as to closely fit the peripheral marginal portions 35a, 35b of lens body 34. In this connection it will be seen that the surface portions 56, 56 of the arms 51 and 52 overlie corresponding peripheral marginal portions 35 of the lens body 34.

The arms 51 and 52 are deformable into the positions shown in FIGS. 3 and 4, respectively, and in use, may be held in the deflected position shown, by holding them with an appropriate surgical instrument during insertion thereof into the eye through an opening such as opening 58 in the cornea. On release, within the eye, the respective arms 51, 52 will spring back into the position thereof shown in FIG. 2 so that an optic 34 may be clamped therebetween.

In order to seat the lens 32 in the anterior chamber, the surgeon first snakes one of the limb portions 46, for example the upper limb 46 in FIG. 3, together with the corresponding arm portion 51 held in the deflected position thereof shown in FIG. 3, through the incision 58. Preferably, in such deflected position the arm 51 substantially overlies limb 46. Then the surgeon can proceed to insert more of the stem 41 through the opening 58 and thereafter, while holding arm 52 in its deflected condition overlying the other limb 46, snake such other limb 46 through the opening 58. Once they are in the anterior chamber 24, the arms 51, 52 are permitted to resiliently snap back to their original undeformed condition, shown in FIG. 2, around an optic 34 which was previously inserted through the opening 58 and is held in place by the surgeon between the arms 51 and 52 as the latter are closed thereabout. The lens body 34 has, according to the preferred embodiment of the present invention, a generally rectangular periphery and the arms 51 and 52 are similarly shaped and can be so connected within the eye that the end portions 53 and 54 thereof abut each other. These end portions preferably have opposed symmetrical inclined surfaces 53a, 54a, and abut each other along those surfaces as seen in FIG. 7.

Preferably, the arms 51 and 52 and the portion of stem 41 therebetween are black in color so as to absorb rather than transmit light rays impinging thereon.

Referring to FIG. 5, a lens body 34 is held in place and surrounded by arms 51, 52 and a central portion of stem 41 of the position-fixation member 40. Arms 51 and 52 in the closed, i.e. undeformed condition thereof, depicted in FIG. 5 exhibit the same generally rectangular shape as the lens body 34 which snugly fits into the grooves 55a at the interior of arms 51, 52 and of said central portion of stem 41.

Referring now to FIG. 6, the lens 32a is of identical construction as the lens 32 of FIGS. 1 and 2 in all respects except that the arms 51a and 52a have a different cross-sectional shape for providing a light mask of a different type. Referring to FIG. 6, the arms 51a, 52a according to this embodiment of this invention, are seen to have transverse cross-sections in the form of prisms 57 on the anterior side thereof so that light rays "b" coming from outside the eye toward the retina in the region of the peripheral marginal portions 35 of optic 34, are deflected, by the prisms 57 overlying such peripheral marginal portions, toward peripheral regions of the anterior or posterior chamber of the eye, as the case may be, but in any event are precluded from impinging on the retina 22 where they might be perceived by the patient as glare.

Thus, according to the present invention, a masking means, as for example a prism 57 or a black colored means 56 surrounding the lens body 34 and overlying, i.e. covering and extending at least slightly inwardly of the peripheral marginal portions 35 of the lens body 34, is provided.

Whether the masking means are in the form of a black-frame as seen in FIG. 5 or in the form of a prism-frame as seen in FIG. 6 or in another form, it is important that the inner peripheral surfaces 56a along at least the opposed marginal regions 35a which are spaced apart a distance substantially less than 5 mm, are located slightly closer to the optical axis 60 than said marginal regions 35a so as to cover the latter and permit only the light rays "a" to pass through to the retina while preventing the light rays "b" from passing through.

The lens body 34 and the position-fixation member 40, may be inserted into the eye through an opening only slightly larger than the width of the lens body 34 by snaking the position-fixation member 40 through the opening 58 in the eye as described above and inserting the lens body 34 through the opening in the eye in a direction substantially parallel to the edge 35a. The lens body 34 and position-fixation member 40 may be held in position in the eye by the surgeon using a second instrument through another opening in the eye usually made for other purposes. After both the lens body 34 and the position-fixation member 40 have been separately inserted into the eye, the surgeon may assemble these parts together in the eye by separating the arms 51, 52, positioning the lens body or optic 34 therebetween, and permitting the arms 51, 52 to resume their normal undeformed condition, as shown in FIG. 2. The lens 32, in assembled condition, may then be seated in the eye as shown in FIG. 1.

It has been found that an optic of no more than 3 mm diameter is necessary for suitable vision. Use of such miniature optic would substantially reduce the size of the incision required and thus reduce the risks involved in the surgery. In the past, however, the glare resulting from light impinging on the peripheral marginal regions of a 3 mm optic has been found so distracting that such optics were not considered viable. According to the present invention however, that disadvantage has been substantially eliminated, since any light rays which would otherwise be deflected from the peripheral marginal regions of such miniature optic toward the retina are now absorbed or redirected by the masking means overlying those peripheral marginal regions. Preferably the lens according to the present invention has a pair of imaginary coordinate axes such as axes X—X and Y—Y which are at right angles to each other and also are at right angles to the optical axis 60. The preferred lens body according to the present invention has a maximum dimension in a direction parallel to one of the said pair of coordinate axes which is about 3 mm. For example, the dimension X of optic 34 in FIG. 8 may be about 3 mm and the dimension Y may be about 5 mm. It will be seen that with a lens body such as shown in FIG. 8, the masking means need only be provided in connection with the marginal peripheral regions 35a and need not be provided along the marginal peripheral regions 35b of the rectangular optic since only the former will normally be within the bundle of light rays impinging on the retina through the pupil of the eye.

From the foregoing description it will be appararent that an intraocular lens constructed in accordance with the invention has the advantage that the lens can be inserted into the eye through an opening which is smaller than the incisions currently required for conventional intraocular lenses. It will be noted that these openings currently must be at least 5 mm in length as determined by the minimum size optic in conventional use.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

I claim:

1. An intraocular lens comprising:
    a lens body for focusing light rays on the retina of an eye, said lens body having a pair of imaginary coordinate axes at right angles to one another and to the optical axis; and
    position-fixation means for seating said lens body in the eye, said position-fixation means separable from said lens body outside the eye and attachable to said lens body inside the eye;
    said lens body having a maximum dimension in the direction parallel to one of its pair of coordinate axes which is substantially less than 5 mm;
    said position-fixation means including masking means overlying at least those portions of the periphery of said lens body which are transverse to said one coordinate axis in the region of said maximum dimension when said position fixation means is attached to said lens body, said position-fixation means further including a central stem portion and a pair of limb portions extending from opposite ends of said stem portion and flexible arm means extending transversely from said stem portion intermediate and in the same direction as said limb portions, said arm means including said masking means and being adapted to be connected with said lens body within the eye.

2. An intraocular lens in accordance with claim 1 in which said maximum dimension is about 3 mm.

3. An intraocular lens in accordance with claim 1 in which said position fixation means includes holding means for engaging at least a portion of the periphery of said lens body for attachment thereto.

4. An intraocular lens in accordance with claim 3 in which said holding means surround the periphery of said lens body.

5. An intraocular lens according to claim 1 in which said masking means is adapted to mask from the retina of the eye, light rays which would otherwise produce a glare effect by being deflected toward the retina from said portion of the periphery of the lens body at an angle different from the angle of the light rays passing through immediately adjacent regions of said lens body.

6. An intraocular lens in accordance with claim 1 in which said masking means comprises optically black means overlying said portions.

7. An intraocular lens according to claim 1 in which said lens body has a maximum dimension in a direction parallel to the other of its coordinate axes which is substantially greater than said first mentioned dimension.

8. In an intraocular lens according to claim 1 in which said arm means substantially surrounds said lens body.

9. In an intraocular lens according to claim 1 in which said arm means comprises a pair of arms each fixed at one of its ends to said position-fixation means and having a free end, said arms adapted to embrace opposite portions respectively of said lens body for securely fastening the latter to said position-fixation means.

10. An intraocular lens according to claim 1 in which said lens body has a miximum dimension in a direction parallel to the other of its pair of coordinate axes which is also substantially less than 5 mm.

11. An intraocular lens comprising:
    a lens body for focusing light rays on the retina of an eye, said lens body having a pair of imaginary coordinate axes at right angles to one another and to the optical axis; and
    position-fixation means for seating said lens body in the eye, said position-fixation means separable from said lens body outside the eye and attachable to said lens body inside the eye;
    said lens body having a maximum dimension in the direction parallel to one of its pair of coordinate axes which is substantially less than 5 mm;
    said position-fixation means including masking means comprising elongated prism means overlying at least those portions of the periphery of said lens body which are transverse to said one coordinate axis in the region of said maximum dimension when said position fixation means is attached to said lens body.

12. An intraocular lens for use as an implant in a human eye having a groove on one side of the iris circumferentially at upper and lower portions of the eye when viewed in cross-section, said lens comprising:

a lens body for focusing light rays on the retina of an eye said lens body having a pair of imaginary coordinate axes at right angles to one another and to the optical axis;

said lens body having a maximum dimension measured in a direction parallel to one of its pair of coordinate axes which is substantially less than 5 mm, whereby said lens body may be inserted into the eye through an incision which is substantially less than 5 mm in length;

position-fixation means for seating said lens body in the eye said position-fixation means being adapted to be inserted through the same small incision in the cornea as said lens body said position-fixation means including generally oppositely disposed first and second position-fixation portions engageable with the respective upper and lower groove portions to fix the lens body with respect to the pupil of the eye and said position-fixation means being separable from said lens body outside the eye and attachable to said lens body inside the eye;

said maximum dimension being so small that a peripheral marginal region of said lens body which extends generally in a direction transverse to said one coordinate axis is located in a path of light rays directed toward the retina when said lens body is seated in the eye whereby said light rays are scattered by said marginal region toward the retina and perceived by the wearer of the lens as glare; and said position-fixation means including masking means overlying said marginal region of said lens body for scattering, in directions away from the retina, light rays, which would otherwise be redirected toward the retina by said marginal region so as to inhibit such light rays from being redirected toward the retina by said marginal region.

* * * * *

UNITED STATES PATENT AND TRADEMARK OFFICE
CERTIFICATE OF CORRECTION

PATENT NO.   :   4,596,578
DATED        :   June 24, 1986
INVENTOR(S)  :   CHARLES D. KELMAN It is certified that error appears in the above-identified patent and that said Letters Patent is hereby corrected as shown below:

Column 6, line 39, change "arm" to --masking--;

Signed and Sealed this

Thirtieth Day of September 1986

[SEAL]

Attest:

Attesting Officer

DONALD J. QUIGG

Commissioner of Patents and Trademarks